(12) United States Patent
Pulitzer, Jr.

(10) Patent No.: US 12,115,008 B1
(45) Date of Patent: Oct. 15, 2024

(54) RACK FOR SURGICAL INSTRUMENT CLEANING

(71) Applicant: Copeland Pulitzer Designs, LLC, New Orleans, LA (US)

(72) Inventor: Sidney Pulitzer, Jr., New Orleans, LA (US)

(73) Assignee: Copeland Pulitzer Designs, LLC, New Orleans, LA (US)

( * ) Notice: Subject to any disclaimer, the term of this patent is extended or adjusted under 35 U.S.C. 154(b) by 0 days.

(21) Appl. No.: 18/379,081

(22) Filed: Oct. 11, 2023

(51) Int. Cl.
| | |
|---|---|
| *A61B 50/22* | (2016.01) |
| *A61B 90/50* | (2016.01) |
| *A61B 90/70* | (2016.01) |
| *B08B 7/02* | (2006.01) |

(52) U.S. Cl.
CPC .............. *A61B 50/22* (2016.02); *A61B 90/50* (2016.02); *A61B 90/70* (2016.02); *B08B 7/028* (2013.01)

(58) Field of Classification Search
CPC ......... A61B 90/50; A61B 90/70; A61B 50/22; B08B 7/028
USPC ....................................................... 211/85.13
See application file for complete search history.

(56) References Cited

U.S. PATENT DOCUMENTS

| | | | | |
|---|---|---|---|---|
| 2,906,410 A | * | 9/1959 | McGuire ................ | A61B 50/20 |
| | | | | D24/228 |
| 3,693,808 A | * | 9/1972 | Rauch ....................... | A47F 5/13 |
| | | | | 211/195 |
| 3,925,014 A | * | 12/1975 | Langdon .................... | A61L 2/26 |
| | | | | 206/370 |
| 4,043,754 A | * | 8/1977 | Sklar ......................... | A61L 2/26 |
| | | | | 248/222.12 |
| 4,229,420 A | * | 10/1980 | Smith ..................... | A61B 50/22 |
| | | | | 606/1 |
| D275,229 S | * | 8/1984 | Sanderson ................... | D24/227 |
| 4,512,466 A | * | 4/1985 | Delang .................. | A61B 50/20 |
| | | | | 206/370 |
| 4,577,755 A | * | 3/1986 | Ramsay .................... | A61L 2/26 |
| | | | | 206/370 |
| 4,641,749 A | * | 2/1987 | Link ...................... | A61B 50/20 |
| | | | | 206/370 |
| 4,865,821 A | * | 9/1989 | Langdon ................ | A61B 50/22 |
| | | | | 422/561 |

(Continued)

FOREIGN PATENT DOCUMENTS

WO    WO-2020062347 A1 *  4/2020  ............. A61B 50/22

*Primary Examiner* — Stanton L Krycinski
(74) *Attorney, Agent, or Firm* — Intellectual Property Consulting, LLC; Jared K. Rovira

(57) ABSTRACT

The present invention is a rack device designed to improve the cleaning process of surgical instruments by efficiently holding many surgical instruments at once. The rack is designed to hold surgical instruments by their finger rings in an open configuration for ease of cleaning the instrument. The racks include end stops on each arm allowing the rack to be turned upside down without the instruments sliding off for better access to the instrument's jaws during manual cand ultrasonic cleaning. The open configuration also allows for easier application of lubricants to the instruments. The rack is made of connected members that form a stable base and instrument holding arms. The rack incorporates a rack holder with a handle and a mount opening that allows the entire rack to be easily transported, placed into a cleaning device, hung up to dry, sprayed with products and easily located when packing surgical kits.

14 Claims, 9 Drawing Sheets

(56) References Cited

U.S. PATENT DOCUMENTS

| | | | | |
|---|---|---|---|---|
| 5,137,151 A * | 8/1992 | Choate | A61B 50/20 | |
| | | | 206/370 | |
| 5,449,069 A * | 9/1995 | Pijanowski | A61B 50/20 | |
| | | | 206/370 | |
| 6,534,000 B1 * | 3/2003 | Michaelson | A61L 2/26 | |
| | | | 422/26 | |
| 7,461,751 B2 * | 12/2008 | Lyons | A61B 50/13 | |
| | | | 211/85.13 | |
| 7,871,581 B1 * | 1/2011 | Coleman | A61B 50/20 | |
| | | | 211/85.13 | |
| 8,753,059 B2 * | 6/2014 | Baker | G16H 20/40 | |
| | | | 211/85.13 | |
| 9,156,571 B2 * | 10/2015 | Ramkhelawan | A61B 50/22 | |
| 9,259,272 B2 * | 2/2016 | Ramkhelawan | B65B 5/08 | |
| 11,678,949 B2 * | 6/2023 | Lees | F16M 11/22 | |
| | | | 269/74 | |
| 11,950,938 B2 * | 4/2024 | Line | B25H 3/04 | |
| 11,969,304 B1 * | 4/2024 | Dawoodjee | A61B 50/20 | |
| 2008/0011699 A1 * | 1/2008 | Lyons | A61B 50/24 | |
| | | | 211/85.13 | |
| 2009/0152414 A1 * | 6/2009 | Lyons | A61B 50/24 | |
| | | | 248/176.1 | |
| 2011/0114522 A1 * | 5/2011 | Alston | A61B 50/22 | |
| | | | 206/370 | |
| 2012/0234781 A1 * | 9/2012 | Cogliano | B25H 3/06 | |
| | | | 211/85.13 | |
| 2013/0074450 A1 * | 3/2013 | Higham | A61B 50/30 | |
| | | | 206/370 | |
| 2013/0105346 A1 * | 5/2013 | Ramkhelawan | A61B 50/33 | |
| | | | 206/370 | |
| 2013/0108503 A1 * | 5/2013 | Ramkhelawan | A61B 50/34 | |
| | | | 422/1 | |
| 2013/0164103 A1 * | 6/2013 | Baker | G16H 20/40 | |
| | | | 414/266 | |
| 2014/0216966 A1 * | 8/2014 | Ramkhelawan | A61B 50/30 | |
| | | | 206/370 | |
| 2015/0374439 A1 * | 12/2015 | Ramkhelawan | A61B 50/34 | |
| | | | 211/85.13 | |
| 2016/0143702 A1 * | 5/2016 | Ramkhelawan | A61B 50/20 | |
| | | | 206/370 | |
| 2023/0134498 A1 * | 5/2023 | Henke | A61B 50/34 | |
| | | | 206/370 | |

* cited by examiner

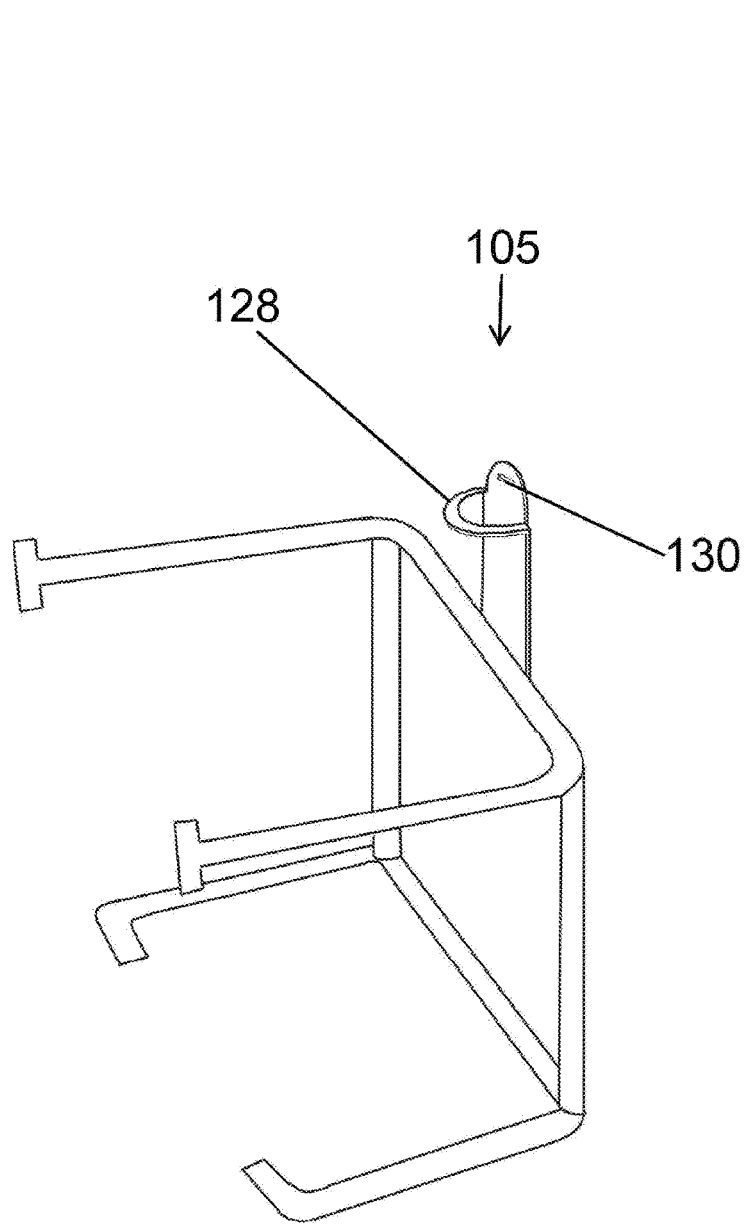
Fig. 2a
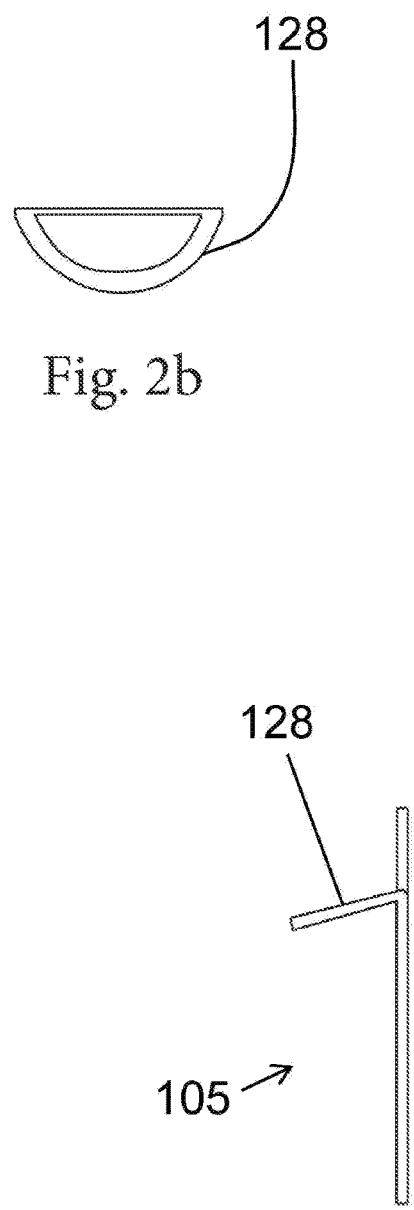
Fig. 2b
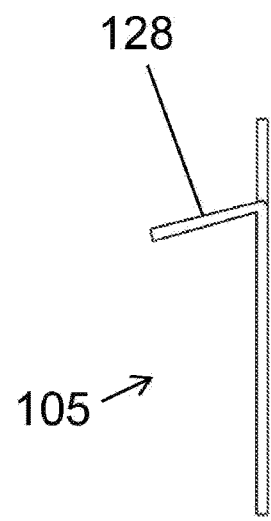
Fig. 2c
Figure 2

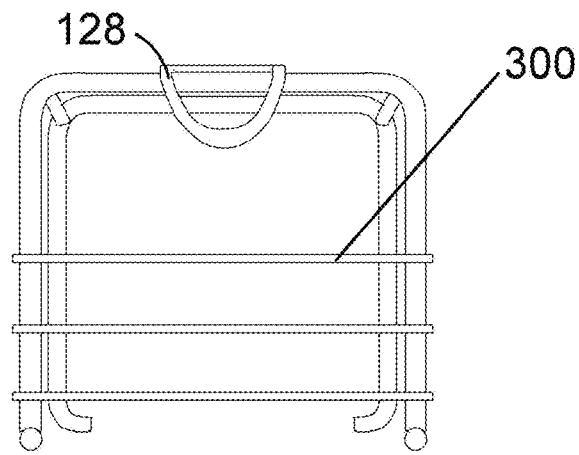
Fig. 3a
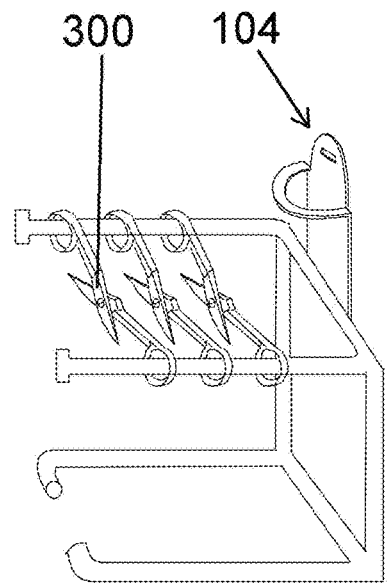
Fig. 3c
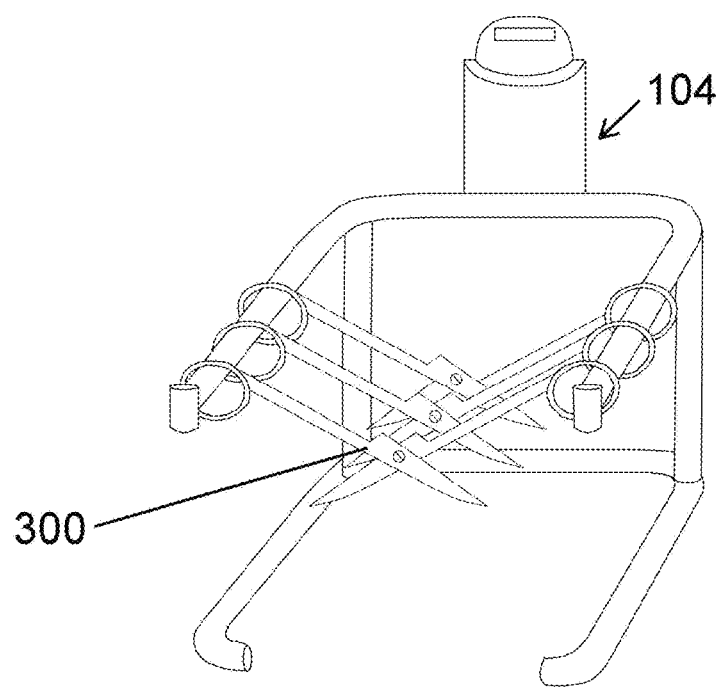
Fig. 3b
Figure 3

Figure 6a-c

RACK FOR SURGICAL INSTRUMENT CLEANING

BACKGROUND

I. Field of the Invention

The present invention relates generally to the cleaning of surgical instruments.

II. General Background

Many surgical operations require a dozen or more surgical instruments. At the scale of large surgical clinics and hospitals, hundreds or thousands of instruments can be used in a single day. In most facilities, staff members must physically hold each instrument open to access the instrument utility area/jaws to remove biological waste before placing the opened instruments in a cleaning device, such as an ultrasonic cleaner. The instruments are then removed from the ultrasonic cleaner and placed in a pile to be sprayed with a lubricant, disinfectant and/or detergent. Instruments are then separated and sorted by type, size, etc. before being packed into surgical packs/kits and then placed in an autoclave for final sterilization. The current method of properly cleaning surgical instruments and preparing these instruments for packs/kits is an intensive and time-consuming process that generates large labor and supply costs. Therefore, a great demand exists for devices and methods that increase the efficiency of the surgical instrument cleaning process and reduce costs for surgical facilities of all sizes.

SUMMARY OF THE INVENTION

In accordance with some embodiments, the present invention is a rack device designed to improve the cleaning process of surgical instruments by efficiently holding many surgical instruments at once. The rack is designed to hold surgical instruments by their finger rings in an open configuration to ensure that the instrument utility areas/jaws are open for optimal manual cleaning. The racks include an end stop on each arm which allows the rack to be turned upside down without the instruments sliding off. This allows for better access to the surgical instruments' utility areas/jaws for better manual cleaning and better cleaning when the rack and instruments are placed open in an ultrasonic cleaner. The rack also makes it easier to apply any lubricant to the hinge screw and open utility area/jaws. The rack is made of connected members that form a stable base. The rack incorporates a rack holder with a handle and a mount opening that allows the entire rack to be easily transported, placed into a cleaning device, hung up to dry, sprayed with products and easily located when packing surgical kits. The rack allows for many surgical instruments to be placed together, thereby increasing the efficiency of multiple steps of the surgical instrument cleaning process. The present invention further includes a method of cleaning surgical instruments using a surgical instrument rack device.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein:

FIG. 2a depicts an angled view of a surgical instrument cleaning rack that emphasizes the rack handle in accordance with an embodiment of the invention.

FIG. 2b depicts a top-down view of a rack handle in accordance with an embodiment of the invention.

FIG. 2c depicts side view of a holder of a surgical instrument cleaning rack in accordance with an embodiment of the invention.

FIG. 3a depicts a top-down view of a rack for cleaning surgical equipment having surgical instruments on the rack on the in accordance with an embodiment of the invention.

FIG. 3b depicts an angled view of a rack for cleaning surgical equipment having surgical instruments on the rack in accordance with an embodiment of the invention.

FIG. 3c depicts a side view of a rack for cleaning surgical equipment having surgical instruments on the rack in accordance with an embodiment of the invention.

Figure 1:
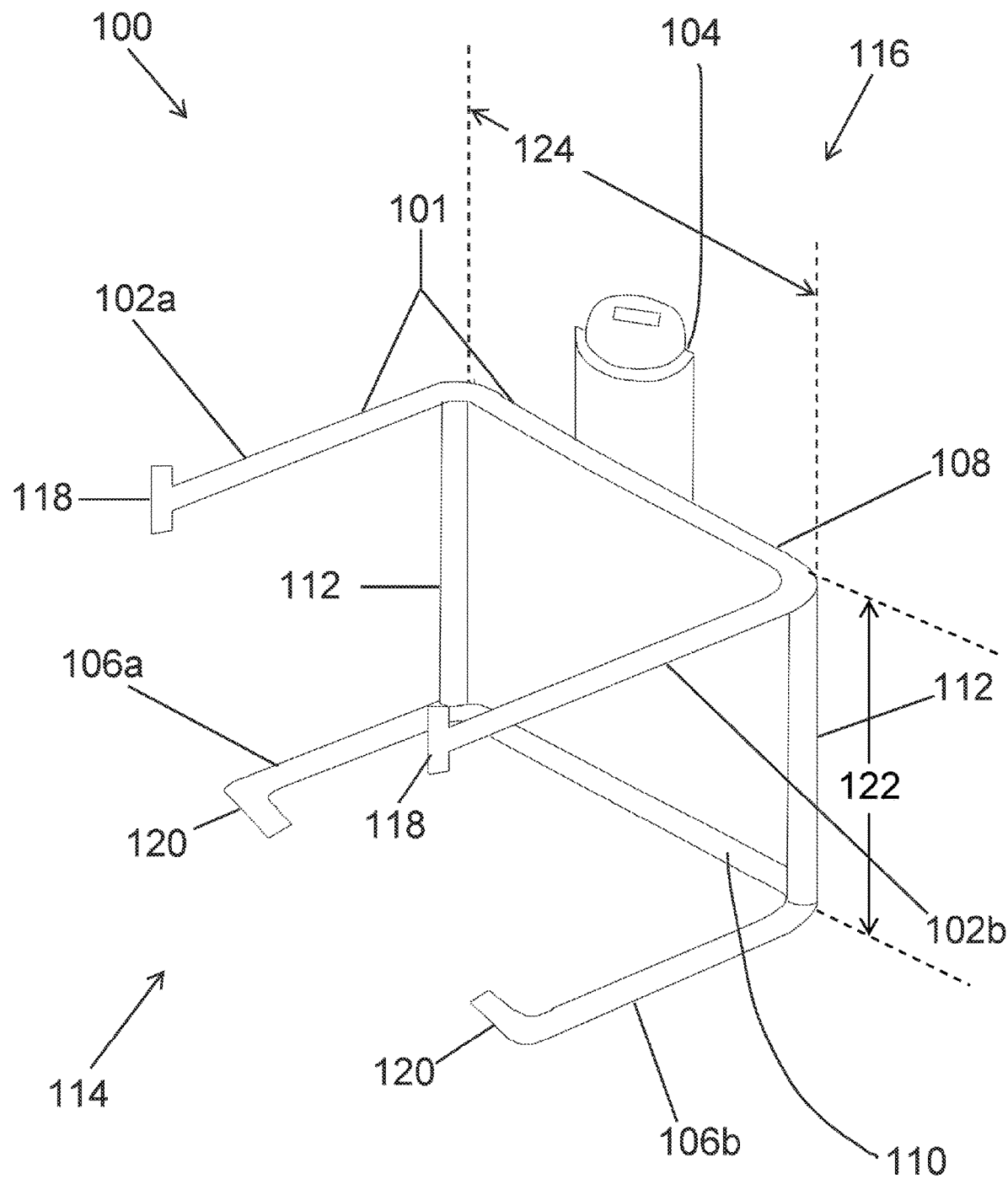
FIG. 1 depicts an isometric view of a surgical instrument cleaning rack in accordance with an embodiment of the invention.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

The embodiments of the disclosure will be best understood by reference to the drawings, wherein like parts are designated by like numerals throughout. It will be readily understood that the components, as generally described and illustrated in the Figures herein, could be arranged and designed in a wide variety of different configurations or be entirely separate. Thus, the following more detailed description of the embodiments of the system and method of the disclosure as represented in the Figures is not intended to limit the scope of the disclosure as claimed, but is merely representative of possible embodiments of the disclosure.

The following description sets forth numerous embodiments and parameters. It should be recognized, however, that such description is not intended as a limitation on the scope of the present invention but is instead provided as a description of exemplary embodiments. Various modifications to the examples described will be readily apparent to those of ordinary skill in the art, and the general principles defined may be applied to other examples and applications without departing from the spirit and scope of the invention. Thus, the present invention is not intended to be limited to the examples described herein but is to be accorded a scope consistent with the claims.

The present invention is a rack device 100 and method 500 of using the rack device designed to improve the cleaning process of surgical instruments for hospital and veterinary surgical facilities. Generally, the rack comprises a number of connected arms that are configured to hold surgical instruments by the instruments' finger rings in an open configuration. The finger rings of surgical instruments are the closed circular structures at the end of the instrument that allow a user to firmly hold and operate the instrument by receiving the user's fingers. The rack system may generally comprise a plurality of labeled skeletal racks for holding medical instruments and a plurality of labeled holders mounted in an optimized grid that allows for organized placement and rapid retrieval of the racks and surgical equipment.

The rack is customizable to be used with any type and size of surgical instruments. Each rack is customized for specific instrument's opened state. For example, "Hemostat" instruments are placed on a specialized rack for "hemostats", "needle drivers" are placed on a rack specifically made for "needle drivers", "curved kelly" instruments are placed on a specialize rack for "curved kellys", etc. The rack holds the instruments open, so the instruments' utility areas/jaws are fully open and accessible for the best manual cleaning and ultrasonic cleaning.

In some embodiments, the invention comprises a rack defined by a plurality of members. The plurality of members may comprise at least two arms, at least two legs, and one of: at least two crossbars and at least one spine, OR; at least one crossbar and at least two spines. The rack may further include a holder.

Referring to the embodiment in FIG. 1, the rack 100 may be a generally cuboid-shaped skeletal structure wherein one side 114 of the cuboid has no edges. The skeletal structure of the rack is made of a plurality of long, narrow members 101 that may have cylindrical, rectangular, triangular or any polygonal shape cross-section. As shown in FIG. 1, the plurality of members 101 may comprise two arms 102a and 102b, two legs 106a and 106b, a first crossbar 108, a second crossbar 110 and two spines 112. The generally rectangular sides of the rack may be defined only on their outer edges by members 101 such that the sides of rack 100 are mostly empty space. A first side 116 of the rack 100 is the generally planar side defined by a first crossbar 108 and two arms 102a and 102b that extend from either end of top crossbar 108. A holder 104 extends from the first crossbar 108 in a direction that may be generally perpendicular to the first side 116. Two spines 112 extend generally from the points where the top crossbar 108 and the two arms 102a and 102b meet, in a direction that is generally perpendicular to the first side 116 and opposite the direction to which holder 104 extends. The ends of spines 112 that are opposite of the first crossbar 108 are both connected to second crossbar 110. Second crossbar 110 extends between the two spines 112 in a direction that is generally parallel to first crossbar 108. Legs 106a and 106b extend generally from the points that the spines 112 and second crossbar 110 meet, in substantially the same direction as arms 102a and 102b and generally perpendicular to second crossbar 110 and spines 112.

Arms 102a and 102b may include stops 118 to prevent instruments from sliding off. Stops 118 may be located at the ends of arms 102a and 102b that are not connected to first crossbar 108. In the embodiment shown FIG. 1, stops 118 may extend in a direction that is parallel to the spines 112. Stops 118 may extend both above and below the plane of first side 116. When stops 118 extend above and below the plane of first side 116, the rack is operable to be turned upside down for better access to the instruments' utility areas/jaws 310 without the instruments sliding off the rack. Stops 118 may be any suitable length that allows for the instruments to be easily placed onto or removed from the rack arms while still preventing the instruments from unintentionally sliding off. In some embodiments, stops 118 may extend in any direction from the free end of arms 102a and 102b. In some embodiments, stops 118 may be circular, oval, cross, or any shape capable of preventing instruments from sliding off of arms 102a and 102b.

The two arms 102a and 102b may be connected to the rest of the structure of rack 100 at only one end in order to allow the finger rings 306 of surgical instruments to slide along the majority of arms 102a and 102b. The arms 102a and 102b, together with end stops 118, work to prevent surgical instruments from closing when they are being manually cleaned or are in an ultrasonic cleaner.

In some embodiments, the arms of the rack may be adjustable in length. Each arm may comprise a base portion and a hollow, slidable portion that slides along the base portion such that slidable portion of the arms may extend away from the rest of rack 100 if more space is needed to store instruments on the arms. The slidable portion of the arm can be slid back along the base portion towards the first crossbar 108 if a more compact orientation of the rack is needed. In some embodiments the arms 102a and 102b are square, rectangular, triangular or any other shape that does not allow the slidable portion of the arm to freely rotate on the base portion. In some embodiments the base portion may contain a number of spring-loaded pegs and the slidable portion may comprise a number of holes that receive the spring-loaded pegs. The spring-loaded pegs and holes work to adjustably secure the slidable arm portion relative to the base portion in one or more positions.

In some embodiments, the first crossbar 108 of the rack may be adjustable in length such that the width between arms 102a and 102b may be adjusted. The first crossbar 108 may comprise a base portion and a hollow, slidable portion that slides along the base portion such that the slidable portion of the first crossbar 108 may extend away from the rest of rack 100. The lengthening of the first crossbar allows for wider instruments to be placed on the rack arms or for the placed instruments to be opened further. The slidable portion of the first crossbar can be slid back along the base portion of the first crossbar towards the holder 104 if a more compact orientation of the rack is desired. In some embodiments the crossbars are square, rectangular, triangular or any other shape that does not allow the slidable portion of the first crossbar 108 to freely rotate on the base portion. In some embodiments the base portion of the first crossbar may contain several spring-loaded pegs and the slidable portion may comprise several apertures that receive the spring-loaded pegs. The spring-loaded pegs and apertures may work to adjustably secure the slidable arm portion relative to the base portion in one or more predetermined positions.

As shown in FIG. 1, the two legs 106a and 106b may be connected to the rest of the structure of rack 100 at only one point. The non-connected ends of legs 106a and 106b may include feet 120 that allow for increased stability and balance of rack 100. As shown in FIG. 1, both feet 120 extend in an inward direction that is generally parallel to second crossbar 110. The inward facing direction of feet 120 prevents components of the batch cleaning devices (such as an ultrasonic cleaner) from being damaged and/or so the feet do not penetrate any basket/holder in the ultrasonic cleaner or other cleaning device when the rack 100 is placed inside.

In some embodiments, the rack 100 may be formed in another shape, such as a cube, trapezoid, or any other suitable shape.

The height 122 of rack 100 is large enough to allow the instrument to be sufficiently opened for cleaning, but short enough so that the entire instrument is submerged when placed in a batch cleaning device, such as an ultrasonic cleaner.

The width 124 of rack 100 may be adjusted according to the size of the surgical instrument to be hung and/or the size of the cleaning device in which it is placed. The width 124 of rack 100 may be any number of widths that accommodate the widths of the finger rings 306 of surgical equipment when the surgical instruments are opened sufficiently to be cleaned. The width 124 of rack 100 may be wide enough to properly open each instrument for cleaning so that the instrument does not fall below the height 122 of the rack, but closed enough together to allow instruments to easily be placed and retrieved on the arms.

The components of rack 100 may be made of any suitable material, for example, stainless steel, plastic, metal alloys, etc. The components of rack 100 are customizable to be used with any form or size of surgical equipment and any type of cleaner. Rack 100 may be used with any form of batch cleaning device, for example, an ultrasonic cleaner, an autoclave, etc. In some embodiments, the rack 100 is sized and shaped to fit into the basket of an ultrasonic cleaner.

In some embodiments, the rack 100 may comprise three, four, five or more legs 106. In some embodiments, one or more bottom crossbars 108 may connect the at least two legs 106 at their open ends, such that the bottom of the rack 100 comprises a square, rectangle or other 4-sided shape, having no break in the shape walls. In some embodiments, one or more additional crossbars may connect the at least two legs 106a and 106b at any point along the distance of the legs 106a and 106b such that the bottom of the rack 100 would comprise, for example, an H-shape, an X shape or a random crisscross pattern. In some embodiments, the bottom of the rack 100 may comprise a plurality of additional crossbars and additional legs so as to define a grid-like pattern.

In some embodiments, the rack 100 can hold thirty to thirty-six instruments. In some embodiments, the rack 100 can hold more than thirty-six instruments. Naturally, the rack 100 may always hold any number of instruments that fit on the arms.

Referring to FIGS. 2a-c, in some embodiments, the rack holder 104 may comprise a handle 128. FIG. 2b depicts handle 128 as generally semicircular; however, handle 128 can be any suitable shape, for example, rectangular, square or any other shape. Handle 128 can define a plurality of openings or, as shown, a single opening. As depicted in the side view shown in FIG. 2c, handle 128 may be angled toward the rack body to increase the leverage of the user. In some embodiments the handle 128 may be perpendicular to rack holder 104. This angle may be from 0-45° from an axis that is normal to the rack holder.

FIG. 3a-c shows examples of rack 100 being partially loaded with of a type of surgical instrument.

Figure 4:
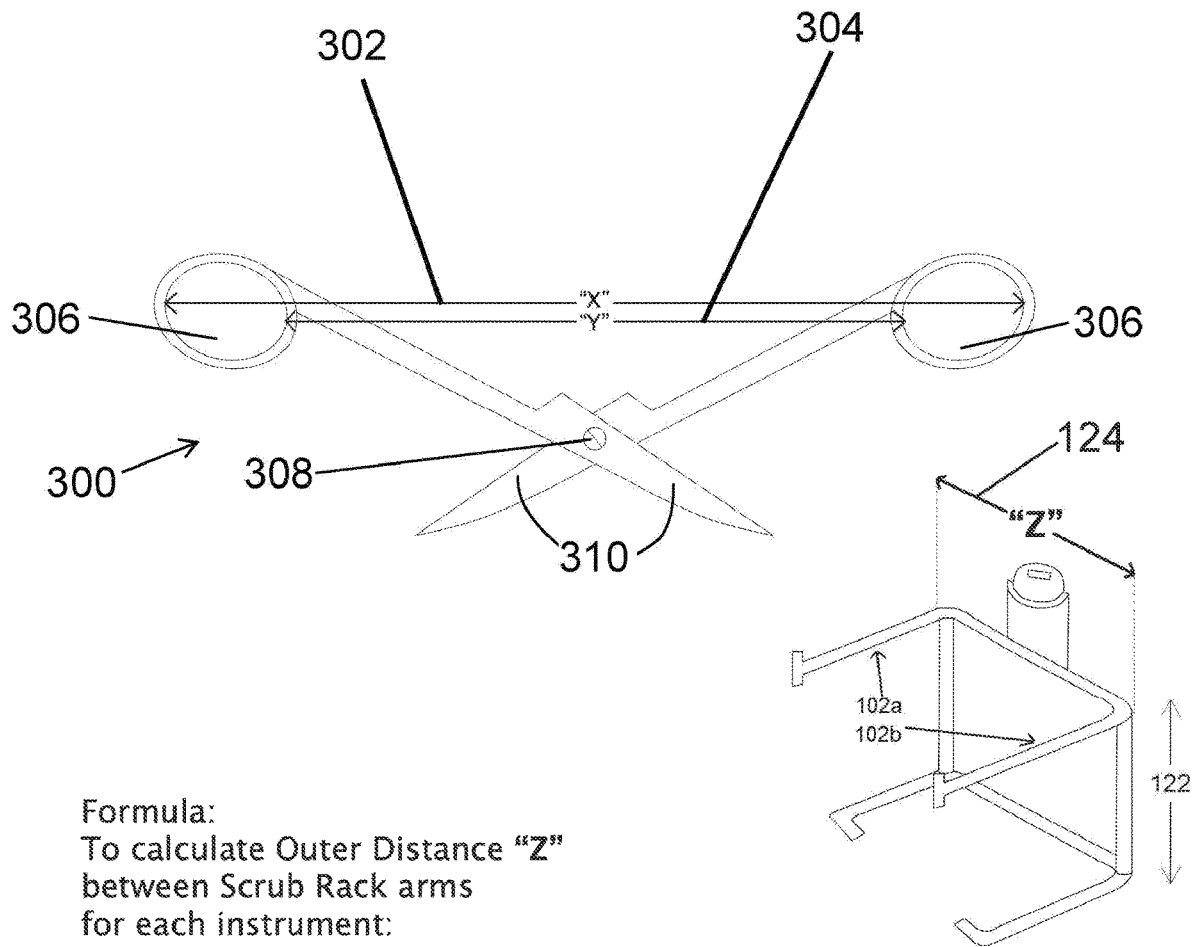
FIG. 4 depicts a formula for calculating the width of the rack's arms for holding surgical instruments to ensure the instruments are both open wide enough to effectively be cleaned and easily stored on and removed from the rack.

Referring to FIG. 4, in some embodiments, the distance between the arms 102a and 102b may be calculated using a formula based on the dimensions of the surgical instruments. The formula to calculate the outer dimensions of the distance between the arms 102 in inches is $$\left[ Z = \frac{(A+B+C)}{3} - 0.1875 \right]$$

wherein Z is the outer distance in inches between the rack arms (also denoted as 124 in this specification);

$$A = X - 0.625; B = Y + 1.25; C = \left[ \frac{X+Y}{2} + 0.3125 \right];$$

X is longest distance 302 between the inside of finger rings 306 of the fully opened instrument; Y is the shortest distance 304 between the inside of finger rings 306 of the fully opened instrument. The formula may alternatively be written as $$\left[ Z = \frac{X}{2} + \frac{Y}{2} + 0.125 \right].$$

Figure 5:
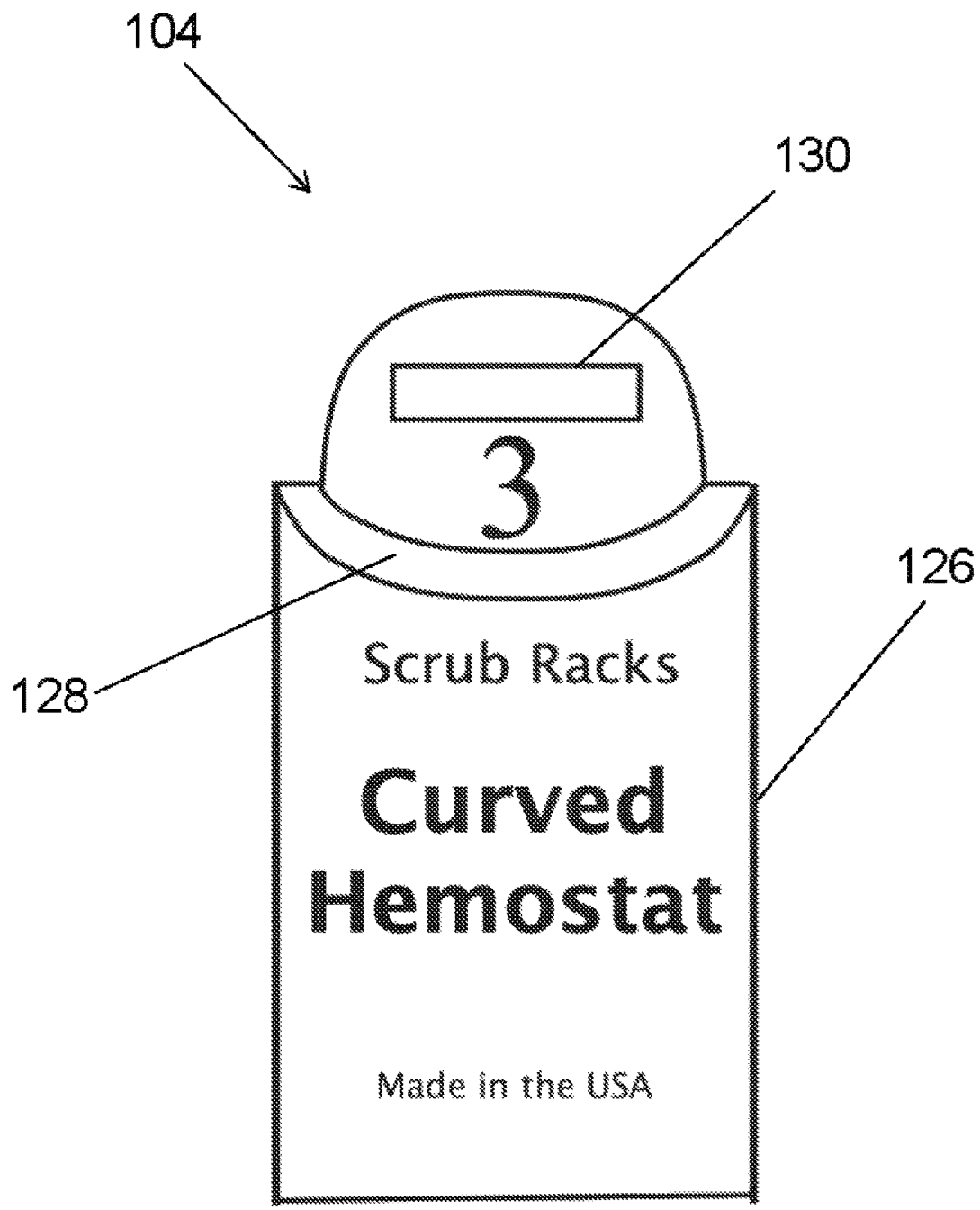
FIG. 5 depicts a front view of a rack holder in accordance with an embodiment of the invention.

Referring to FIG. 5, in some embodiments, rack holder 104 may generally comprise body 126, a handle 128 and a mount opening 130. Handle 128 may be held by a user for transportation of rack 100. As discussed above, handle 128 may be angled toward the rack body. Mount opening 130 also operates to receive a hook, lip, protrusion, prong or any form of hanging implement such that the rack 100 can be hung. Body 126 is configured to have a label etched in the surface of the body that faces rack 100. The label can designate any desired information, however, the exemplary use is to designate the type of surgical instrument for which the rack is designed and any other information a surgical facility desires (codes, storage information, instrument type, size etc.). The labels may operate to inform users of the type of instrument stored on the rack to simplify the surgical kit packing process and to help prevent errors. In some embodiments, label body 126 may be configured to receive a removable label, such as an adhesive backed label. In some embodiments, the label body 126 may be rectangular, cylindrical, half-cylindrical, square or any other suitable shape. Handle 128 may be any suitable shape such as semi-circular, square, rectangular or any polygonal shape.

Figure 6:
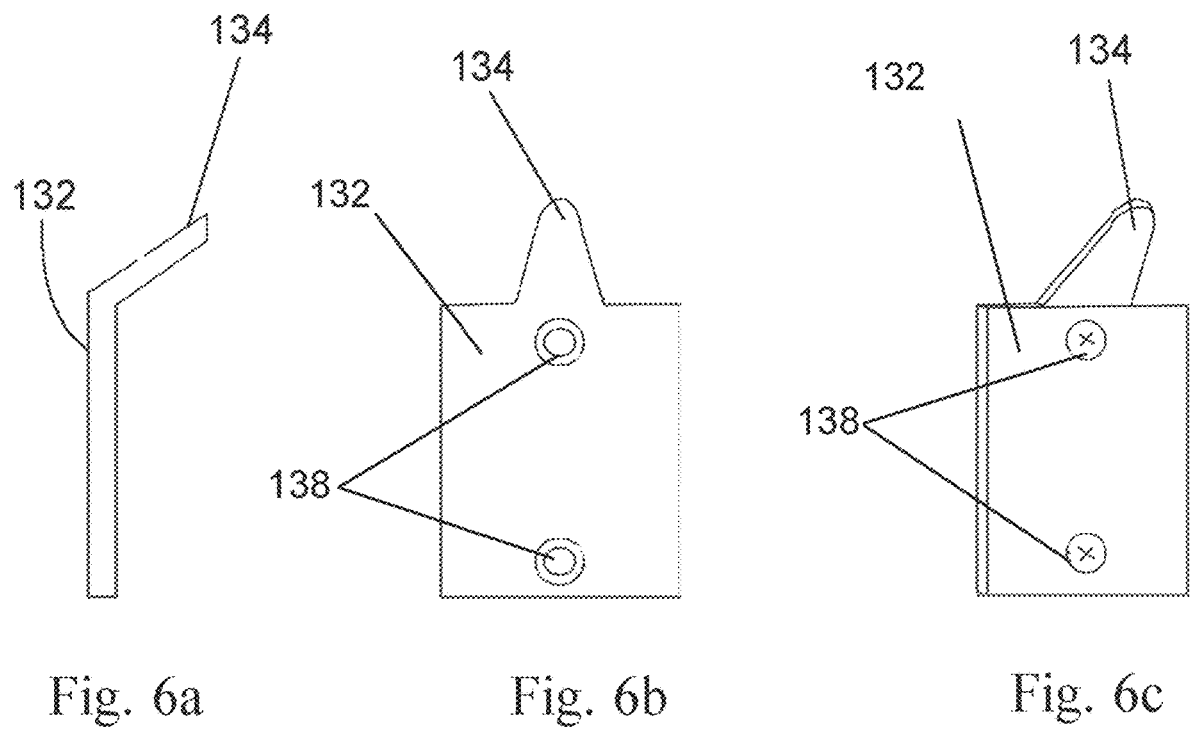
FIG. 6a-c depicts multiple views of a mount for hanging a rack in accordance with an embodiment of the invention.

Referring to FIGS. 6a-c, in some embodiments, the invention includes a mount 132 that includes a prong 134 extending away from mount 132 at an angle. Prong 134 is configured to fit into mount opening 130 of holder 104 in order to hang rack 100. Mount 132 includes at least one opening 138 configured to receive a fastener. Mount 132 may be configured to have a surface capable of being etched or labeled. The labeling may be used for any purpose, such as corresponding a specific mount to a specific rack or type of rack.

Figure 7:
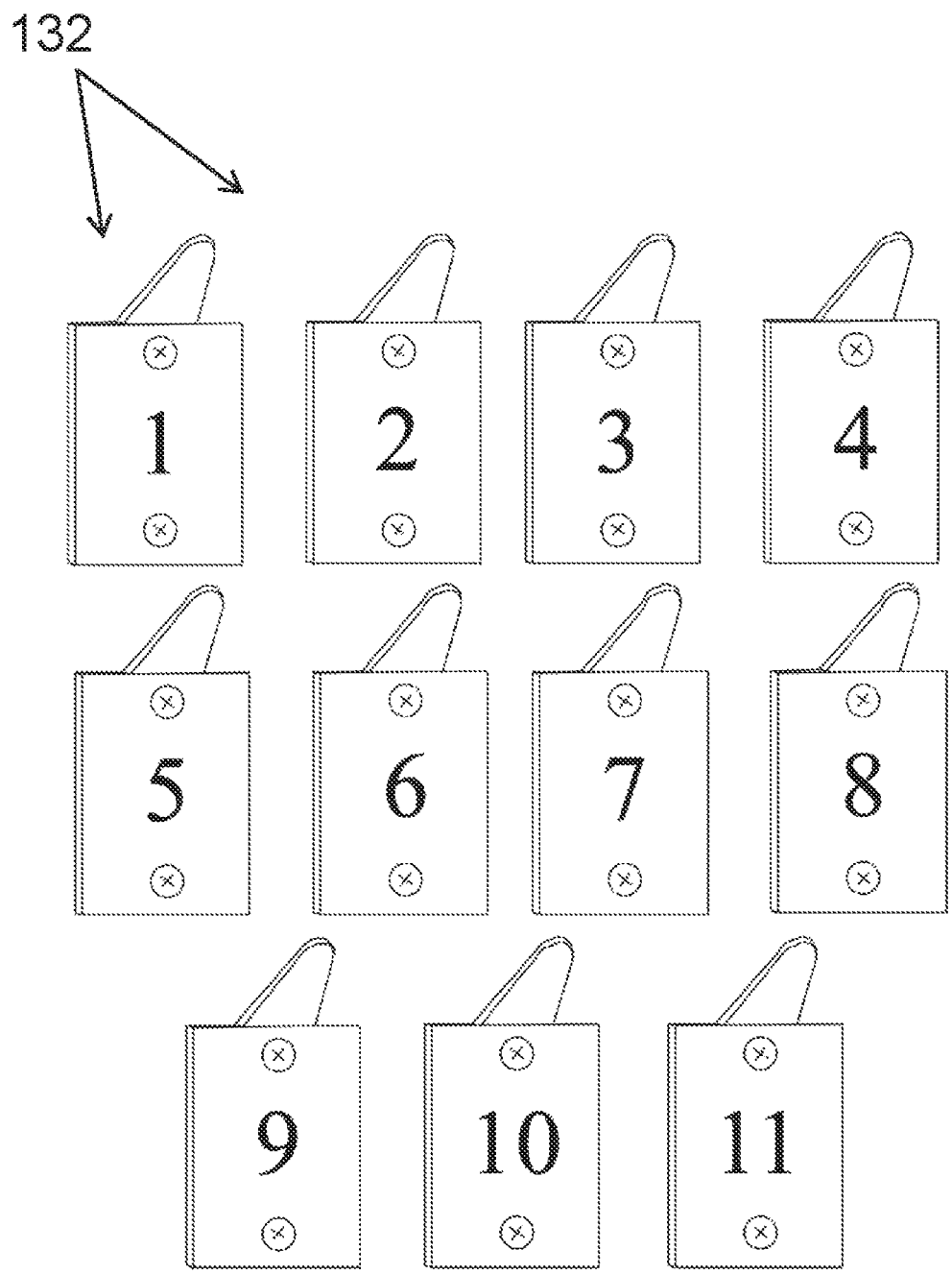
FIG. 7 depicts a plurality of fixed mounting brackets in accordance with an embodiment of the invention.

Referring to FIG. 7, in some embodiments, the invention includes a plurality of mounts 132 to hold a plurality of racks 100.

Figure 8:
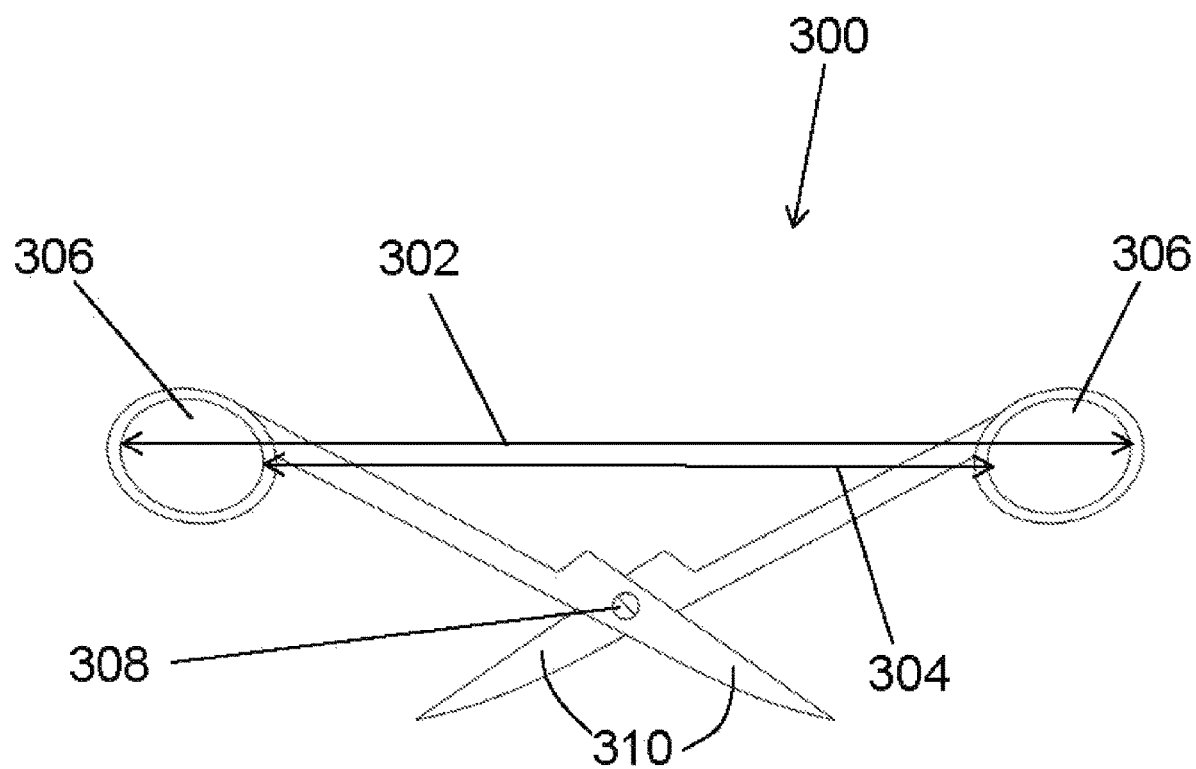
FIG. 8 depicts an example of a surgical instrument that may be used on/with the invention in accordance with an embodiment of the invention.

FIG. 8 depicts an example of a surgical instrument 300 that rack 100 can hold. Surgical instrument 300 may comprise finger rings 306, a hinge, a hinge screw 308 and a utility area/jaws 310. The instrument may have a longest distance 302 between the inside of finger rings 306 of the fully opened instrument. The instrument may have a shortest distance 304 between the inside of finger rings 306 of the fully opened instrument.

Figure 9:
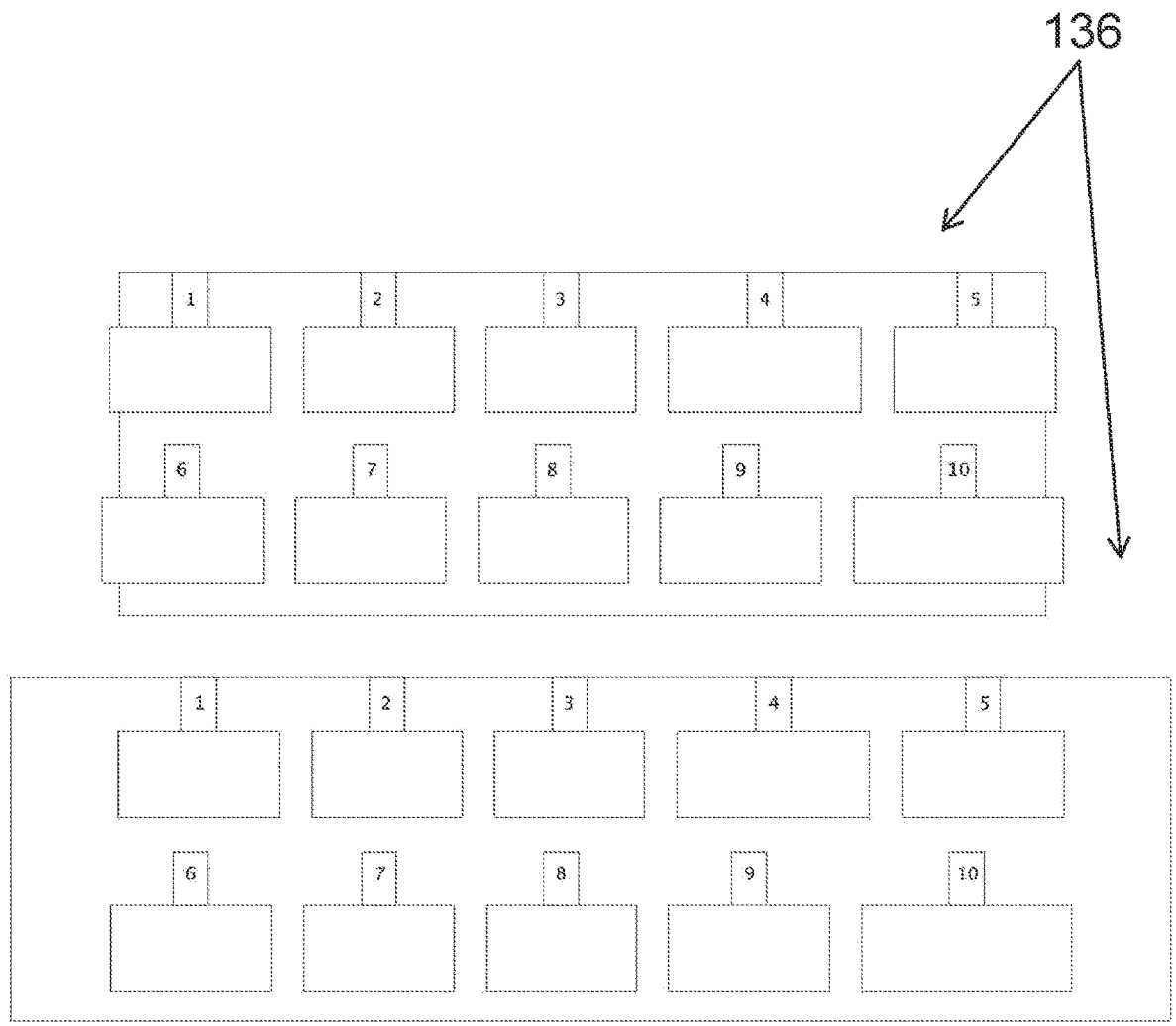
FIG. 9 depicts a board arranged with a plurality of mounts arranged in a manner that organizes a plurality of racks in varying sizes.

Referring to FIG. 9, in some embodiments, the invention comprises a board 136 including a plurality of mounts 132. The plurality of mounts 132 are arranged on board 136 to optimize the storage of racks 100. Board 136 allows many racks to be hung for storage, cleaning, spraying, etc.

At the end of a surgery day, all used surgical instruments are opened and placed on each instrument's rack ("hemostat" instruments are placed on a specialized rack for "hemostats", "needle drivers" are placed on a rack specifically made for "needle drivers", "curved kelly" instruments are placed on a specialized rack for "curved kellys", etc.) that holds the instruments open so the instruments' edges are fully open and accessible.

In some embodiments, the invention further comprises a method 500 of using rack 100 to clean surgical instruments. Method 500 allows for the scrubbing, brushing etc. across the surfaces of many instruments at once, rinsing of many instruments in the sink at once and transporting many instruments at once. The method described below may be modified to remove any number of steps and is still in accordance with the embodiments of this invention.

The method 500 comprises the following steps:

The first method step 510, one or more surgical instruments is opened and placed on rack 100.

Next, in method step 520, one or more loaded or partially loaded racks 100 are placed and the hung instruments are cleaned at the same time. In some embodiments of step 520, method step 520 may include method step 520a wherein the rack 100 is placed handle side up and the tops of the instruments are cleaned, which may be followed by method step 520b wherein then the rack 100 is flipped over and the utility areas/jaws of the instruments are manually cleaned. Manual cleaning may include, for example, scrubbing and/or brushing.

Next, in method step 530, one or more loaded or partially loaded racks 100 are placed in an surgical instrument ultrasonic cleaner with all instruments open and exposed to the cleaning action of the cleaner.

Next, in method step 540, the instruments on each rack are sprayed with lubricant on the instrument's utility areas/jaws and hinges. The instruments may be sprayed with any form of substance, for example, detergent, bleach, disinfectant or a cleaning product.

Next, in method step 550, the one or more racks 100 are placed on a surface or hung up in an organized manner, allowing a user to organize the instruments into to surgical packs or kits with other designated instruments that are needed for the next operation.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

The invention claimed is:

1. A device for holding surgical instruments comprising:
a rack, comprising:
at least a first arm and a second arm;
two or more legs;
wherein the at least a first arm and a second arm are connected to the two or more legs by one or more substantially vertical spines;
wherein the first arm is operable to hold a first finger ring of one or more instruments;
and wherein the second arm is operable to hold a second finger ring of the one or more instruments;
wherein the width between the first arm and the second arm allows the first arm to hold the first finger ring of the one or more instruments and the second arm to hold the second finger ring of the one or more instruments at the same time;
wherein when the first arm is holding the first finger ring of the one or more instruments and the second arm is holding the second finger ring of the one or more instruments at the same time, the width between the first arm and the second arm allows a jaw of the one or more instruments to be open.

2. The device of claim 1, wherein at least one of the first arm and the second arm comprise an end stop.

3. The device of claim 2, wherein the end stop extends from the at least one of the first arm and the second arm in at least two directions.

4. The device of claim 2, wherein the end stop extends from the at least one of the first arm and the second arm in a direction that is perpendicular to the at least one of the first arm and the second arm.

5. The device of claim 2, wherein the end stop is operable to allow the rack to be inverted and to help prevent the first finger ring and the second finger ring of the one or more instruments from sliding off the first arm and the second arm, respectively, in the inverted state.

6. The device of claim 1, wherein at least one of the legs comprises a foot.

7. The device of claim 6, wherein the foot is attached to a free end of the at least one of the legs and wherein the foot extends in a direction that is inward relative to the rack.

8. The device of claim 1, wherein the outer width dimension between the first arm and the second arm does not allow the ends of the jaws of the one or more instruments to extend below the legs of the rack when the first arm is holding the first finger ring of the one or more instruments and the second arm is holding the second finger ring of the one or more instruments at the same time.

9. The device of claim 1, wherein the rack further comprises a handle.

10. The device of claim 1, wherein the rack further comprises a body extending from the rack; wherein the body comprises a handle and an opening;
and wherein the body comprises a substantially flat surface operable to display information.

11. The device of claim 1, wherein the distance in inches between the first arm and the second arm is half the longest distance between the inside of the finger rings of the fully opened surgical instrument plus half the shortest distance between the inside of the finger rings of the fully opened surgical instrument plus one eight of an inch.

12. The device of claim 1, wherein the rack is sized to fit in the basket of an ultrasonic cleaner.

13. A device for holding surgical instruments comprising:
a skeletal rack comprising:
a first side defined by a first crossbar, a first arm and a second arm; wherein the first arm and the second arm comprise an end stop;
a rack holder extending from the first crossbar; the rack holder comprising a handle and an opening for receiving a mount projection;
at least one spine extending from the first crossbar in a direction that is perpendicular to a plane defined by the first arm, the second arm and the first crossbar;
the at least one spine connecting the first crossbar to a second crossbar; the second crossbar extending in a direction that is parallel to the first crossbar;
two or more legs extending from the second crossbar; wherein the legs comprise feet at the ends of the legs that are opposite to the second crossbar;
wherein the at least one spine comprises a vertical extending rod.

14. The device of claim 13, wherein the cross-sectional diameter of the arms is less than the diameter of a finger ring of a surgical instrument.

* * * * *